United States Patent
Harada et al.

(10) Patent No.: US 11,142,506 B2
(45) Date of Patent: Oct. 12, 2021

(54) DIARYL CARBONATE AND METHOD FOR PRODUCING THE SAME, AND METHOD FOR PRODUCING AN AROMATIC POLYCARBONATE RESIN

(71) Applicant: MITSUBISHI GAS CHEMICAL COMPANY, INC., Tokyo (JP)

(72) Inventors: Hidefumi Harada, Hyogo (JP); Jungo Taguchi, Saitama (JP); Yoshinori Isahaya, Ibaraki (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 16/738,226

(22) Filed: Jan. 9, 2020

(65) Prior Publication Data

US 2020/0140399 A1     May 7, 2020

Related U.S. Application Data

(62) Division of application No. 15/766,208, filed as application No. PCT/JP2016/080174 on Oct. 12, 2016, now abandoned.

(30) Foreign Application Priority Data

Oct. 14, 2015    (JP) ................................ 2015-202941

(51) Int. Cl.
| | |
|---|---|
| *C07D 265/26* | (2006.01) |
| *C07C 68/08* | (2006.01) |
| *C08G 64/30* | (2006.01) |
| *C07C 69/96* | (2006.01) |
| *C08G 64/04* | (2006.01) |
| *B01D 3/42* | (2006.01) |
| *B01D 9/00* | (2006.01) |
| *C07B 61/00* | (2006.01) |

(52) U.S. Cl.
CPC .......... *C07D 265/26* (2013.01); *B01D 3/4211* (2013.01); *B01D 9/0031* (2013.01); *C07C 68/08* (2013.01); *C07C 69/96* (2013.01); *C08G 64/04* (2013.01); *C08G 64/30* (2013.01); *C07B 61/00* (2013.01)

(58) Field of Classification Search
CPC ..... B01D 3/4211; B01D 9/0031; C07C 68/00; C07C 68/06; C07C 68/08; C07C 69/96; C07B 61/00
See application file for complete search history.

(56) References Cited

U.S. PATENT DOCUMENTS 5,980,445 A    11/1999   Mizukami et al.
2007/0270604 A1*   11/2007   Fukuoka ................ C07C 68/06
                                                                 558/274

FOREIGN PATENT DOCUMENTS

| EP | 1829854 | * | 9/2007 |
|---|---|---|---|
| EP | 1961731 | | 8/2008 |
| JP | 10-152455 | | 6/1998 |
| JP | 10-152456 | | 6/1998 |
| JP | H11-228504 A | | 8/1999 |
| JP | 2000-063332 | | 2/2000 |
| JP | 2003-226751 | | 8/2003 |

OTHER PUBLICATIONS

JP 10-152455-English machine translation (Jun. 9, 1998).*
JP2000-063332 to Yoshihia-English machine translation (Feb. 29, 2000).*
JPH 11-228504-English machine translation (Aug. 24, 1999).*
JPH 09-110805 to Inaba-English machine translation (Apr. 28, 1997).*
European Extended Search Report, European Patent Office, U.S. Appl. No. 16/855,401, dated Apr. 25, 2019.
International Search Report, issued in International Bureau of WIPO, Application No. PCT/JP2016/080174, dated Jan. 10, 2017.
International Preliminary Report on Patentability, issued in International Bureau of WIPO, Application No. PCT/JP2016/080174, dated Apr. 17, 2018.
Notice of Reason of Refusal, Japanese Patent Office, Application No. 2017-545205, dated Jul. 21, 2020, English translation.
Principle of Chemical Engineering, p. 296 (2007), with English translation.
Chinese Office Action issued with respect to Chinese application 201680054798.5, dated Nov. 27, 2020, with English translation.
Principle of Chemical Engineering, p. 296 (2007).
Chine Office Action issued with respect to Chinese application 201680054798.5, dated Nov. 27, 2020.

* cited by examiner

*Primary Examiner* — Valerie Rodriguez-Garcia
(74) *Attorney, Agent, or Firm* — Greenblum & Bernstein, P.L.C.

(57) ABSTRACT

Disclosed are a diaryl carbonate containing a compound of the following formula (I) in an amount of less than 1,000 ppm by mass, and a method for producing the same:

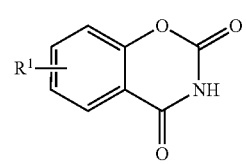

(I)

wherein $R^1$ represents a hydrogen atom, a halogen atom, an alkyl group, an alkoxy group, an aryl group, or an aryloxy group. Disclosed methods include reacting urea with an alkyl alcohol to provide a dialkyl carbonate; reacting the dialkyl carbonate with an aryl alcohol to provide an alkylaryl carbonate; subjecting the alkylaryl carbonate to disproportionation to yield a mixture comprising a diaryl carbonate; and purifying the mixture.

3 Claims, 1 Drawing Sheet

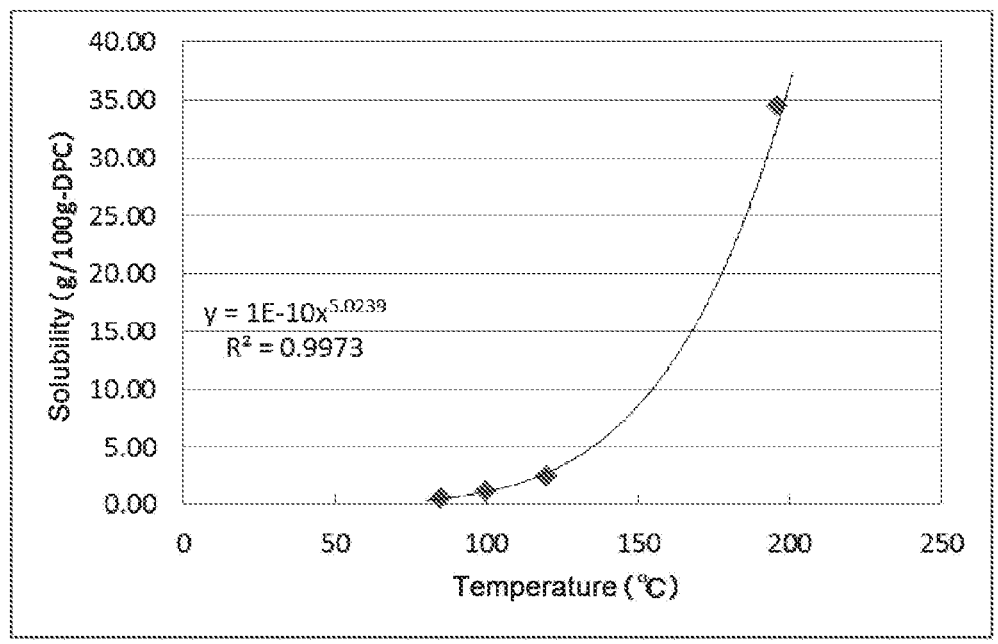

DIARYL CARBONATE AND METHOD FOR PRODUCING THE SAME, AND METHOD FOR PRODUCING AN AROMATIC POLYCARBONATE RESIN

This is a divisional application of U.S. patent application Ser. No. 15/766,208, filed Apr. 5, 2018, which is a National Phase application of International Application No. PCT/JP2016/080174, filed on Oct. 12, 2016, which claims the benefit of Japanese Patent Application No. 2015-202941, filed on Oct. 14, 2015. The entire disclosure of each of the above-identified applications, including the specification, drawings, and claims, is incorporated herein by reference in its entirety.

FIELD OF THE INVENTION

The present invention relates to a diaryl carbonate and a method for producing the same. In addition, the present invention relates to a method for producing an aromatic polycarbonate resin by a melt transesterification method using the diaryl carbonate.

BACKGROUND ART

A diaryl carbonate is a compound which is advantageously used as a raw material for a polycarbonate produced by a melt transesterification method, and has conventionally been produced by a reaction of an aromatic hydroxy compound and phosgene. However, the production of a diaryl carbonate using phosgene is disadvantageous not only in that phosgene is highly toxic and highly likely to cause the apparatuses used in the production to suffer corrosion, but also in that a great amount of an alkali is required for neutralizing hydrogen chloride by-produced during the reaction. Therefore, a method for producing a diaryl carbonate without using phosgene is desired, and some attempts to develop such a method have been made.

Among the attempts, a method suitable for producing a diaryl carbonate especially from an industrial point of view has been proposed in which a dialkyl carbonate is obtained from urea and an alkyl alcohol having 3 to 6 carbon atoms, and then the dialkyl carbonate and an aromatic hydroxy compound are subjected to transesterification to obtain an alkylaryl carbonate, and the obtained alkylaryl carbonate is subjected to disproportionation, producing a diaryl carbonate (see, for example, patent document 1). By reusing the by-produced alkyl alcohol as a raw material for the dialkyl carbonate in this method, the method can produce a diaryl carbonate from inexpensive urea and aromatic hydroxy compound.

PRIOR ART REFERENCE

Patent Document

Patent document 1: Japanese Unexamined Patent Publication No. Hei 10-152456

SUMMARY OF THE INVENTION

Problems to be Solved by the Invention

The diaryl carbonate produced by the above-mentioned method has a problem in that the diaryl carbonate has mixed thereinto the by-produced nitrogen-containing compound and, when such a diaryl carbonate is used in the subsequent process for producing an aromatic polycarbonate resin by a melt transesterification method, the nitrogen-containing compound inhibits a polymerization reaction between the diaryl carbonate and an aromatic dihydroxy compound. In view of the above-mentioned problem, an object of the present invention is to provide a diaryl carbonate containing a reduced amount of the nitrogen-containing compound which inhibits a polymerization reaction.

Means for Solving the Problems

The present inventors have conducted extensive and intensive studies with a view toward solving the above-mentioned problems. As a result, it has been found that, by using a diaryl carbonate containing a nitrogen-containing compound in an amount of less than a specific amount, the above-mentioned problems accompanying the method for producing an aromatic polycarbonate resin by a melt transesterification method can be solved, and the present invention has been completed. In addition, the present inventors have found a method for producing the above diaryl carbonate.

The present invention is as follows.

[1] A diaryl carbonate containing a compound of the following formula (I) in an amount of less than 1,000 ppm by mass:

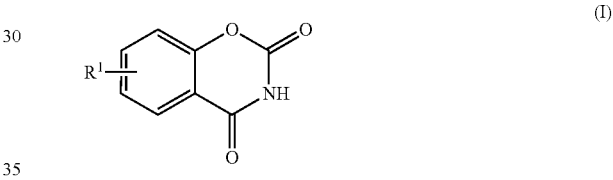

wherein $R^1$ represents a hydrogen atom, a halogen atom, an alkyl group, an alkoxy group, an aryl group, or an aryloxy group.

[2] A method for producing the diaryl carbonate according to item [1] above, wherein the method comprises:

a first step of reacting urea with an alkyl alcohol to yield a first reaction mixture containing a dialkyl carbonate;

a second step of reacting the dialkyl carbonate in the first reaction mixture with an aromatic hydroxy compound to yield a second reaction mixture containing an alkylaryl carbonate;

a third step of subjecting the alkylaryl carbonate in the second reaction mixture to disproportionation to yield a third reaction mixture containing a diaryl carbonate; and a fourth step of purifying the third reaction mixture, wherein the third reaction mixture further contains the compound of the formula (I) in an amount of 1,000 ppm by mass or more.

[3] The method according to item [2] above, wherein the fourth step comprises a distillation step of, using a distillation column, obtaining the diaryl carbonate containing the compound of the formula (I) in an amount of less than 1,000 ppm by mass from the top of the column and obtaining a mixture having concentrated the compound of the formula (I) from the bottom of the column, wherein the distillation step is conducted under the following conditions (a) and (b):

(a) that the pressure at the top of the distillation column is 0.01 to 10 kPa, and (b) that the reflux ratio is 2 to 20.

[4] The method according to item [3] above, which further comprises a fifth step of filtering off the compound of the formula (I) which is precipitated from the concentrated mixture at a temperature in the range of from 80 to 230° C.

[5] The method according to item [4] above, which further comprises a recycling step (sixth step) of recovering the compound of the formula (I) filtered off in the fifth step and bringing the filtrate back to the fourth step.

[6] The method according to any one of items [2] to [5] above, wherein the alkyl alcohol used in the first step is an alkyl alcohol having 3 to 6 carbon atoms.

[7] A method for producing an aromatic polycarbonate resin, wherein the method comprises performing melt polycondensation in the presence of a transesterification catalyst using the diaryl carbonate according to item [1] above and an aromatic dihydroxy compound.

Effects of the Invention

In the production of an aromatic polycarbonate by a melt transesterification method, by using a diaryl carbonate containing the compound of the formula (I) in an amount of less than 1,000 ppm by mass, the polymerization time can be reduced, as compared to that in the production of an aromatic polycarbonate using a diaryl carbonate produced by a conventional method. Therefore, the present invention has a remarkable effect from an industrial viewpoint.

BRIEF DESCRIPTION OF THE DRAWING

FIG. 1 A graph showing a change with the temperature of the solubility of 2H-1,3-benzoxazine-2,4(3H)-dione (BOD) in diphenyl carbonate (DPC).

MODE FOR CARRYING OUT THE INVENTION

The terms used in the present invention are defined as described below unless otherwise specified.

In the present specification, the term "step" means not only an independent step but also a combination of steps which cannot be clearly distinguished from one another as long as a desired purpose of the steps is achieved. Further, the range of values indicated using the preposition "to" means a range of values including the respective values shown before and after the preposition "to" as the minimum value and the maximum value. Furthermore, with respect to the amount of the component of a mixture, when a plurality of materials corresponding to the components are present in the mixture, the amount of the components in the mixture means the total amount of the materials present in the mixture unless otherwise specified.

In the present invention, the term "halogen atom" means a fluorine atom, a chlorine atom, a bromine atom, or an iodine atom.

In the present invention, the term "alkyl group" means a monovalent group of linear, branched, or cyclic saturated aliphatic hydrocarbon unless otherwise specified. Examples of "alkyl groups having 1 to 10 carbon atoms" include a methyl group, an ethyl group, a n-propyl group, an isopropyl group, a cyclopropyl group, a n-butyl group, an isobutyl group, a s-butyl group, a t-butyl group, a cyclobutyl group, a pentyl group, a cyclopentyl group, a hexyl group, a cyclohexyl group, a heptyl group, a cycloheptyl group, an octyl group, a cyclooctyl group, a nonyl group, a cyclononyl group, a decyl group, and a cyclodecyl group (including their isomers). These include examples of "alkyl groups having 1 to 6 carbon atoms" and examples of "alkyl groups having 3 to 6 carbon atoms".

In the present invention, the term "alkoxy group" means a —O-alkyl group (wherein the alkyl is as defined above) unless otherwise specified. In the present invention, preferred examples of alkoxy groups include "alkoxy groups having 1 to 6 carbon atoms", such as a methoxy group, an ethoxy group, a n-propyloxy group, an isopropyloxy group, a cyclopropyloxy group, a n-butyloxy group, an isobutyloxy group, a s-butyloxy group, a t-butyloxy group, a cyclobutyloxy group, a pentyloxy group, a cyclopentyloxy group, a hexyloxy group, and a cyclohexyloxy group (including their isomers).

In the present invention, the term "aryl group" means a monovalent group of monocyclic or polycyclic aromatic hydrocarbon unless otherwise specified. In the present invention, preferred examples of aryl groups include "aryl groups having 6 to 10 carbon atoms", such as a phenyl group, a naphthyl group, and an anthryl group. An especially preferred example of aryl group is a phenyl group. The "aryl group" may be substituted with an alkyl group having 1 to 6 carbon atoms.

In the present invention, the term "aryloxy group" means a —O-aryl group (wherein the aryl is as defined above). In the present invention, preferred examples of aryloxy groups include "aryloxy groups having 6 to 10 carbon atoms", such as a phenoxy group, a naphthyloxy group, and an anthryloxy group. An especially preferred example of aryloxy group is a phenoxy group.

<Diaryl Carbonate>

The present invention is directed to a diaryl carbonate containing a compound of the following formula (I):

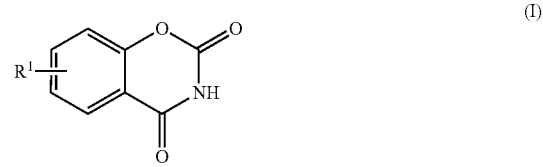

(I)

wherein $R^1$ represents a hydrogen atom, a halogen atom, an alkyl group, an alkoxy group, an aryl group, or an aryloxy group
in an amount of less than 1,000 ppm by mass.

The diaryl carbonate of the present invention is specifically a diaryl carbonate which is represented by the following formula (6):

ArO—CO—OAr     (6)

wherein Ar represents a phenyl group, or a phenyl group substituted with a halogen atom, an alkyl group, an alkoxy group, an aryl group, or an aryloxy group, and which contains the compound of the formula (I) in an amount of less than 1,000 ppm by mass.

When Ar is a phenyl group, the diaryl carbonate of the present invention is diphenyl carbonate (which is frequently referred to as "DPC" in the present specification) containing the compound of the formula (I) wherein $R^1$ is a hydrogen atom (2H–1,3-benzoxazine-2,4(3H)-dione (which is frequently referred to as "BOD" in the present specification)), in an amount of less than 1,000 ppm by mass.

When Ar is a phenyl group substituted with a halogen atom, an alkyl group, an alkoxy group, an aryl group, or an aryloxy group, the diaryl carbonate of the present invention is that containing the compound of the formula (I) wherein $R^1$ is the same as the substituent for Ar, in an amount of less than 1,000 ppm by mass.

A specific embodiment of the present invention is DPC containing BOD in an amount of less than 1,000 ppm by mass.

The amount of the compound of the formula (I) contained in the diaryl carbonate of the present invention is 0.1 to less than 1,000 ppm by mass, preferably 900 ppm by mass or less, more preferably 800 ppm by mass or less, especially preferably 700 ppm by mass or less.

The diaryl carbonate of the present invention is produced by a method using urea, an alkyl alcohol, and an aromatic hydroxy compound, typically by the below-described <Method for producing a diaryl carbonate> of the present invention.

<Method for Producing a Diaryl Carbonate>

The present invention is also directed to a method for producing a diaryl carbonate which contains a compound of the following formula (I):

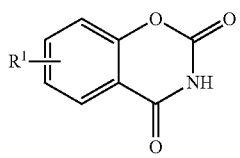
(I)

wherein $R^1$ represents a hydrogen atom, a halogen atom, an alkyl group, an alkoxy group, an aryl group, or an aryloxy group
in an amount of less than 1,000 ppm by mass. The method comprises:

a first step of reacting urea with an alkyl alcohol to yield a first reaction mixture containing a dialkyl carbonate;

a second step of reacting the dialkyl carbonate with an aromatic hydroxy compound to yield a second reaction mixture containing an alkylaryl carbonate;

a third step of subjecting the alkylaryl carbonate to disproportionation to yield a third reaction mixture containing a diaryl carbonate; and a fourth step of purifying the reaction mixture, wherein the third reaction mixture further contains the compound of the formula (I) in an amount of 1,000 ppm by mass or more.

(First Step)

In the first step, a reaction of urea with an alkyl alcohol is performed to yield a first reaction mixture containing a dialkyl carbonate. The alkyl alcohol used in the first step is represented by the following formula (1):

R—OH (1)

wherein R represents an alkyl group, preferably an alkyl group having 3 to 6 carbon atoms.

Examples of the alkyl alcohols include n-propanol, isopropanol, n-butanol, isobutanol, s-butanol, t-butanol, 1-pentanol, 2-pentanol, 3-pentanol, 2-methyl-1-butanol, 2-methyl-2-butanol, 3-methyl-1-butanol, 3-methyl-2-butanol, 2,2-dimethyl-1-propanol, cyclopentanol, 1-hexanol, 2-hexanol, 3-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, and 3-ethyl-1-butanol.

In the reaction of urea with an alkyl alcohol, an alkyl carbamate of the following formula (2):

RO—CO—NH$_2$ (2)

wherein R is as defined above is first yielded, and then further reacted with the alkyl alcohol to yield a dialkyl carbonate of the following formula (3):

RO—CO—OR (3)

wherein R is as defined above.

Generally, a reaction in which urea is transformed to an alkyl carbamate is fast, and a reaction in which the alkyl carbamate is transformed to a dialkyl carbonate is slow. Preferred reaction conditions for the respective stages of reactions are different from each other. Therefore, when the reactions are conducted in a continuous manner, it is necessary to perform the reactions in two separate stages, but, when the reactions are conducted in a batch-wise manner, the reactions can be successively performed in the same reactor.

With respect to the stage in which an alkyl carbamate is produced from urea, the reaction is fast and therefore can be conducted at a relatively low temperature. A preferred reaction temperature is 100 to 200° C. When the reaction in this stage is performed at too high a temperature, a side reaction disadvantageously occurs. The reaction pressure is preferably atmospheric pressure to about 2 MPa. In this reaction, ammonia is formed and therefore, by providing the system with, for example, a pressure control valve, the reaction may be conducted while appropriately removing ammonia from the system so as to maintain the inside of the system at a predetermined pressure. For selectively removing only ammonia from the system, it is preferred that the reactor is provided with a distillation column at the upper portion thereof. The reaction time is about 1 to 4 hours. The reaction can be performed while allowing an inert gas, such as nitrogen gas, to flow through the reaction system, and the reaction is satisfactorily fast such that it generally does not need such inert gas. Further, an inert solvent can be used in the reaction.

With respect to the stage in which a dialkyl carbonate is produced from the alkyl carbamate, the reaction is slightly slow, and hence a preferred reaction temperature is 180 to 260° C. The reaction pressure is preferably atmospheric pressure to about 3 MPa. Also in this reaction, ammonia is formed and therefore, by providing the system with, for example, a pressure control valve, the reaction may be conducted while appropriately removing ammonia from the system so as to maintain the inside of the system at a predetermined pressure. For selectively removing only ammonia from the system, it is preferred that the reactor is provided with a distillation column at the upper portion thereof. The reaction time is about 1 to 20 hours. If necessary, the reaction can be performed while allowing an inert gas, such as nitrogen gas, to flow through the reaction system for facilitating the removal of ammonia.

The above-mentioned reactions can be conducted either in the same reactor or in separate reactors, and, in both cases, it is preferred that the same catalyst is used in the reactions. With respect to the catalyst used in the reactions, various catalysts are described in, for example, Japanese Unexamined Patent Publication Nos. Sho 55-102542, Sho 57-26645, and Sho 57-175147, and any of the catalysts described can be used in the present invention. Of these, especially, an oxide, a hydroxide, a halide, an inorganic salt, an organic acid salt, an alkoxide, or an alkylalkoxide of at least one metal selected from the group consisting of zinc, magnesium, lead, copper, tin, and titanium is preferably used. Specific examples thereof include zinc oxide, magnesium oxide, lead acetate, copper acetate, dibutyltin oxide, and tetrabutoxytitanium. Further, organic amines, such as 1,4-diazabicyclo[2.2.2]octane and 1,8-diazabicyclo[5.4.0]undecene, can be used.

The alkyl alcohol of the formula (1) is used in an amount of about 0.5 to 10 mol, relative to 1 mol of urea. The amount of the catalyst is preferably 0.1 to 20 mol %, based on 1 mol of urea. In this reaction, a preferred alcohol is an alkyl alcohol having 3 or more carbon atoms. An alkyl alcohol having less than 3 carbon atoms disadvantageously lowers the yield and increases the pressure during the reaction.

After completion of the reaction, a first reaction mixture containing a dialkyl carbonate can be obtained. The first reaction mixture can further contain, for example, the unreacted alkyl alcohol, an alkyl carbamate which is an intermediate, and the catalyst. Before subjected to the second step, at least part of the unreacted alkyl alcohol, alkyl carbamate as an intermediate, and catalyst may be removed from the first reaction mixture by distillation. The separated alkyl alcohol, alkyl carbamate, and catalyst can be reused in the reaction.

(Second Step)

In the second step, a reaction of the dialkyl carbonate in the first reaction mixture with an aromatic hydroxy compound is performed to yield a second reaction mixture containing an alkylaryl carbonate. The aromatic hydroxy compound used in the second step is represented by the following formula (4):

Ar—OH  (4)

wherein Ar is as defined above.

Examples of the aromatic hydroxy compounds include phenol, p-chlorophenol, 2,4-dichlorophenol, o-cresol, m-cresol, p-cresol, 2,4-dimethylphenol, 3,4-dimethylphenol, 3,5-dimethylphenol, o-ethylphenol, m-ethylphenol, p-ethylphenol, p-n-propylphenol, p-isopropylphenol, p-n-butylphenol, p-isobutylphenol, p-t-butylphenol, 4-hydroxyanisole, p-phenylphenol, and p-phenoxyphenol.

Specifically, in the second step, the dialkyl carbonate of the formula (3) is reacted with the aromatic hydroxy compound of the formula (4) to yield an alkylaryl carbonate of the following formula (5):

ArO—CO—OR  (5)

wherein Ar and R are as defined above.

This reaction is conducted at a reaction temperature of about 160 to 250° C. under a pressure of about 0.01 to 1 MPa. Further, this reaction is an equilibrium reaction, and therefore it is preferred to withdraw the by-produced alkyl alcohol to advance the reaction. The reaction may be conducted either in a reactor provided with a distillation column at the upper portion thereof, or in a reactive distillation column.

When the second step is performed using a reactive distillation column, preferred is a distillation column which has the number of plates of 3 or more, including a condenser plate and a reboiler plate, and which enables continuous distillation. For example, any plate column using a bubble cap tray, a sieve tray, or a valve tray, or any packed column which is packed with a packing, such as Sulzer laboratory packing, Sulzer packing, Mellapak, Dixon packing, or Rasching ring, can be used. Of these, a plate column is more preferably used. The number of plates means the number of actual plates in the case of a plate column, and means the number of theoretical plates in the case of a packed column.

For example, more preferred is a method in which, while continuously feeding the dialkyl carbonate, aromatic hydroxy compound, and catalyst to the highest plate of the distillation column, the by-produced alkyl alcohol is continuously withdrawn from the top of the column and the alkylaryl carbonate is continuously withdrawn from the bottom of the column. The reaction time is about 1 to 10 hours. The reaction can be performed while allowing an inert gas, such as nitrogen gas, to flow through the reaction system, but generally, the reaction does not need such inert gas.

With respect to a preferred catalyst in this reaction, any catalyst generally known as a transesterification catalyst can be used, but, particularly, an alkoxide, an aryloxide, an alkyl-substituted oxide, or an acetylacetonato of a metal selected from titanium, aluminum, gallium, tin, and yttrium, or an adduct of the above compound and another compound is preferably used.

Among the above catalysts, a titanium compound of the following formula:

$Ti(OX)_4$, or $Ti(OX)_4 \cdot XOH$ wherein X represents an alkyl group having 3 to 6 carbon atoms, or aryl group or an adduct thereof is especially preferably used.

Examples of the catalysts represented by the above formula include titanium tetrapropoxide, titanium tetrabutoxide, titanium tetraamyloxide, titanium tetrahexyloxide, titanium tetraphenoxide, and titanium tetra(4-methylphenoxide) (including their isomers).

Alternatively, with respect to the catalyst, a tin compound of the following formula:

$Y^1_2SnO$, $Y^1_2Sn(OY^2)_2$, or $Sn(OY^2)_4$ wherein $Y^1$ represents an alkyl group having 1 to 10 carbon atoms, and $Y^2$ represents an alkyl group having 3 to 6 carbon atoms is preferably used.

Examples of the catalysts represented by the above formula include diethyltin oxide, dipropyltin oxide, dibutyltin oxide, diamyltin oxide, dioctyltin oxide, dibutyldibutoxytin, diethyldiamyloxytin, tetrabutoxytin, and tetraisoamyloxytin (including their isomers). Alternatively, a compound which is capable of being transformed into the above compound under the reaction conditions can be used.

In this reaction, the aromatic hydroxy compound of the formula (4) is used in an amount of about 0.2 to 10 mol, relative to 1 mol of the dialkyl carbonate of the formula (3), more preferably in an amount about 1 to 5 times the mole of the dialkyl carbonate. The amount of the catalyst is preferably 0.01 to 10 mol %, based on 1 mol of the dialkyl carbonate of the formula (3).

After completion of the reaction, a second reaction mixture containing an alkylaryl carbonate can be obtained. In this reaction, generally, an alkylaryl carbonate as well as a diaryl carbonate are likely to be formed. Accordingly, the second reaction mixture can further contain, for example, the diaryl carbonate, by-produced alkyl alcohol, and catalyst. After completion of the second step, the alkylaryl carbonate may be separated from the second reaction mixture by distillation, but it is preferred that the second reaction mixture as such is subjected to the third step.

(Third Step)

In the third step, the alkylaryl carbonate is subjected to disproportionation to yield a disproportionation reaction mixture containing a diaryl carbonate and the compound of the formula (I) in an amount of 1,000 ppm by mass or more. Specifically, in the third step, the alkylaryl carbonate of the formula (5) is subjected to disproportionation to yield a third reaction mixture containing a diaryl carbonate of the following formula (6):

ArO—CO—OAr      (6)

wherein Ar is as defined above
and the compound of the formula (I) in an amount of 1,000 ppm by mass or more. This reaction is conducted at a reaction temperature of about 160 to 250° C. under a pressure of about 0.01 to 1 MPa. Further, this reaction is an equilibrium reaction, and therefore it is preferred to withdraw the by-produced dialkyl carbonate to advance the reaction. The reaction may be conducted either in a reactor provided with a distillation column at the upper portion thereof, or in a reactive distillation column.

When the third step is performed using a reactive distillation column, like the second step, preferred is a distillation column which has the number of plates of 3 or more, including a condenser plate and a reboiler plate, and which enables continuous distillation. Especially, a packed column is more preferably used. For example, more preferred is a method in which, while feeding the alkylaryl carbonate to the side portion of the distillation column, the by-produced dialkyl carbonate is continuously withdrawn from the top of the column, and the third reaction mixture containing the diaryl carbonate and the compound of the formula (I) is continuously withdrawn from the bottom of the column. The reaction time is about 1 to 10 hours. The reaction can be performed while allowing an inert gas, such as nitrogen gas, to flow through the reaction system, but generally, the reaction does not need such inert gas.

In this reaction, if necessary, a transesterification catalyst is used. The examples and amount of the transesterification catalyst are the same as those mentioned above in connection with the second step.

(Fourth Step)

In the fourth step, the third reaction mixture obtained in the third step is purified. The third reaction mixture generally can contain the diaryl carbonate and the compound of the formula (I) as well as, for example, the unreacted alkylaryl carbonate and catalyst. The purification is preferably performed using a distillation column.

For example, the purification of the third reaction mixture comprises a distillation step of obtaining the diaryl carbonate containing the compound of the formula (I) in an amount of less than 1,000 ppm by mass from the top of the distillation column and obtaining a mixture having concentrated the compound of the formula (I) and the like from the bottom of the column, wherein the distillation step is conducted under conditions such (a) that the pressure at the top of the distillation column is 0.01 to 10 kPa, and (b) that the reflux ratio at the top of the distillation column is 0.5 to 20, preferably 2 to 20, further preferably 4 to 20. When the reflux ratio at the top of the column is less than 2, it is likely that the content of the compound of the formula (I) in the diaryl carbonate is 1,000 ppm by mass or more. On the other hand, when the reflux ratio is more than 20, the efficiency of the purification is likely to be reduced. The distillation temperature is generally 100 to 300° C., preferably 120 to 280° C.

The fourth step may comprise the separation/removal step for the catalyst as a part of the purification step. The separation/removal step for the catalyst is preferably performed before the distillation step. For example, the separation/removal step can be performed by continuously feeding the third reaction mixture to a catalyst separation column (distillation column) so as to subject the mixture to flash distillation. The alkylaryl carbonate, diaryl carbonate, and the compound of the formula (I) are continuously withdrawn from the top of the catalyst separation column. The catalyst and the diaryl carbonate in a small amount are continuously withdrawn from the bottom of the column. The liquid withdrawn from the top of the column can be used in the distillation step as the third reaction mixture. Alternatively, the liquid withdrawn from the top of the column may be subjected to the below-mentioned recovery step for the alkylaryl carbonate, and then used in the distillation step as the third reaction mixture. The liquid withdrawn from the bottom of the column can be brought back to the second step and/or third step and reused as a catalyst.

The flash distillation is performed at a temperature in the range of from 100 to 300° C. under a pressure in the range of from 0.001 to 0.1 MPa.

Further, the fourth step may comprise the recovery step for the alkylaryl carbonate as a part of the purification step. The recovery step is preferably performed before the distillation step and after the separation/removal step for the catalyst. For example, the liquid withdrawn from the top of the catalyst separation column may be continuously fed to an alkylaryl carbonate recovery column (distillation column) to separate low-boiling point components including the alkylaryl carbonate. The diaryl carbonate and the compound of the formula (I) are continuously withdrawn from the bottom of the column, and the alkylaryl carbonate is continuously withdrawn from the top of the column. The liquid withdrawn from the bottom of the column can be used in the distillation step as the third reaction mixture. The liquid withdrawn from the top of the column can be brought back to the third step and reused as a raw material.

In the recovery step for the alkylaryl carbonate, the distillation temperature is generally 100 to 300° C., preferably 120 to 280° C. The pressure is preferably 0.001 to 0.1 MPa.

(Fifth Step/Sixth Step)

The production method of the present invention may further comprise, as a fifth step, the step of cooling the compound of the formula (I), which is gradually concentrated and built up on the bottom of the column while performing the fourth step, to any temperature in the range of from 80 to 230° C., preferably 82 to 150° C., more preferably 82 to 100° C., and filtering off the compound. The temperature may be selected according to the solubility of the compound of the formula (I) in a diaryl carbonate for reference, for example, the solubility of BOD in DPC shown in FIG. 1. By virtue of this, the compound of the formula (I) built up on the bottom of the column can be efficiently removed. With respect to the method for the filtration, there is no particular limitation, and a general method may be used. However, a method using, for example, natural filtration, filtration under reduced pressure, filtration under pressure, or centrifugal filtration is preferred. With respect to the filter medium, there is no particular limitation, and a general filter medium can be used. However, a filter medium made of a plastic fiber, such as polypropylene or Teflon (registered trademark), and a filter medium made of a metal, such as a stainless steel fiber, are preferred from the viewpoint of being free of a disadvantage, such as falling of fiber.

Further, the filtrate obtained in the fifth step can be brought back to the fourth step, for example, brought as the third reaction mixture back to any one of the separation/removal step for the catalyst, the recovery step for the alkylaryl carbonate, and the distillation step in the fourth step. The production method of the present invention may comprise such a recycling step as a sixth step.

In each of the steps in the production method of the present invention, the reaction can be conducted in the presence of an inert solvent, in the presence of an inert gas, and/or under a pressure using an inert gas. Needless to say, it is preferred that the individual raw materials used in the present invention have high purity. Specifically, the purity is preferably 95 to 100%. Further, the purity of the dialkyl carbonate which is an intermediate is preferably 90 to 100%.

The continuous production method of the present invention can optionally comprise a known step in addition to the above-mentioned steps. For example, the catalyst separation step described in Japanese Unexamined Patent Publication No. 2004-323384 may be provided between the transesterification step and the disproportionation step so that a liquid containing most of the alkylaryl carbonate and a liquid containing the catalyst are separated from each other, feeding the liquid containing the alkylaryl carbonate to the disproportionation step.

<Method for Producing an Aromatic Polycarbonate Resin>

The present invention is also directed to a method for producing an aromatic polycarbonate resin, wherein the method comprises performing melt polycondensation in the presence of a transesterification catalyst using the diaryl carbonate of the present invention and an aromatic dihydroxy compound. The method for producing an aromatic polycarbonate resin in accordance with a melt polymerization method is known, and the diaryl carbonate of the present invention can be used in such a known method.

As examples of the aromatic dihydroxy compounds used in the method for producing an aromatic polycarbonate resin of the present invention, there can be mentioned compounds of the following general formula (II).

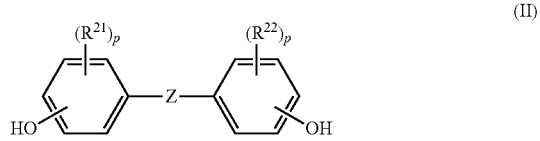

(II)

In the general formula (II), each of the two phenylene groups may be independently a p-phenylene group, a m-phenylene group, or an o-phenylene group. However, both the two phenylene groups are preferably a p-phenylene group.

In the general formula (II), each of $R^{21}$ and $R^{22}$ is independently a halogen atom, a nitro group, an amino group, an alkyl group, an alkoxy group, an aryl group, or an aryloxy group. Specific preferred examples of $R^{21}$ and $R^{22}$ include fluorine, an amino group, a methoxy group, a methyl group, and a phenyl group.

Each of p and q independently represents an integer of 0 to 4, preferably an integer of 0 to 2. Z represents a single bond or a divalent group selected from the group of linking groups (III) shown below. In the group of linking groups (III), each of $R^{33}$ and $R^{34}$ independently represents a hydrogen atom, an alkyl group, or an aryl group, or $R^{33}$ and $R^{34}$ together form an aliphatic ring.

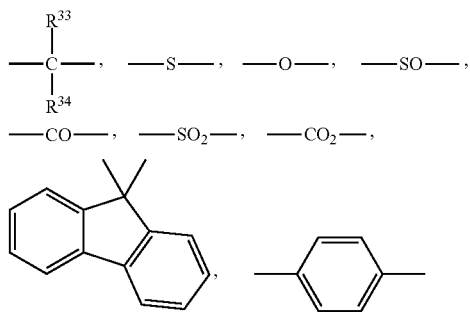

(III)

Specific examples of the aromatic dihydroxy compounds include bis(4-hydroxyphenyl)methane, 1,1-bis(4-hydroxyphenyl)ethane, 1,2-bis(4-hydroxyphenyl)ethane, 2,2-bis(4-hydroxyphenyl)propane, 2,2-bis(4-hydroxy-3-isopropylphenyl)propane, 2,2-bis(4-hydroxyphenyl)butane, 2,2-bis(4-hydroxyphenyl)octane, 2,2-bis(3-t-butyl-4-hydroxyphenyl)propane, 2,2-bis(3-bromo-4-hydroxyphenyl)propane, bis(4-hydroxyphenyl)phenylmethane, 1,1-bis(4-hydroxyphenyl)-1-phenylethane, bis(4-hydroxyphenyl)diphenylmethane, 2,2-bis(4-hydroxy-3-methylphenyl)propane, 1,1-bis(4-hydroxy-3-t-butylphenyl)propane, 2,2-bis(3-cyclohexyl-4-hydroxyphenyl)propane, 1,1-bis(3-cyclohexyl-4-hydroxyphenyl)cyclohexane, 2,2-bis(3,5-dimethyl-4-hydroxyphenyl)propane, 2,2-bis(4-hydroxy-3-phenylphenyl)propane, 2,2-bis(3-cyclohexyl-4-hydroxyphenyl)propane, 2,2-bis(4-hydroxy-3-bromophenyl)propane, 2,2-bis(3,5-dibromo-4-hydroxyphenyl)propane, 1,1-bis(4-hydroxyphenyl)cyclopentane, 1,1-bis(4-hydroxyphenyl)cyclohexane, 2,2-bis(4-hydroxy-3-methoxyphenyl)propane, 1,1-bis(4-hydroxyphenyl)-3,3,5-trimethylcyclohexane, 4,4'-dihydroxydiphenyl ether, 4,4'-dihydroxybiphenyl, 9,9-bis(4-hydroxyphenyl)fluorene, 9,9-bis(4-hydroxy-3-methylphenyl)fluorene, 1,1-bis(4-hydroxyphenyl)cyclohexane, 1,1-bis(4-hydroxyphenyl)cyclopentane, 4,4'-dihydroxy-3,3'-dimethylphenyl ether, 4,4'-dihydroxyphenyl sulfide, 4,4'-dihydroxy-3,3'-dimethyldiphenyl sulfide, 4,4'-dihydroxydiphenyl sulfoxide, 4,4'-dihydroxy-3,3'-dimethyldiphenyl sulfoxide, 4,4'-dihydroxydiphenyl sulfone, 4,4'-dihydroxy-3,3'-dimethyldiphenyl sulfone, 2,2'-diphenyl-4,4'-dihydroxydiphenyl sulfonyl, 2,2'-dimethyl-4,4'-dihydroxydiphenyl sulfonyl, 1,3-bis {2-(4-hydroxyphenyl)propyl}benzene, 1,4-bis{2-(4-hydroxyphenyl)propyl}benzene, 1,4-bis(4-hydroxyphenyl)cyclohexane, 1,3-bis(4-hydroxyphenyl)cyclohexane, 4,8-bis(4-hydroxyphenyl)tricyclo[5.2.1.0$^{2,6}$]decane, 4,4'-(1,3-adamantanediyl)diphenol, and 1,3-bis(4-hydroxyphenyl)-5,7-dimethyladamantane.

Of these, 2,2-bis(4-hydroxyphenyl)propane (hereinafter, frequently referred to as "bisphenol A" or "BPA") is more preferred for the reasons that, for example, BPA has high stability, and further BPA having impurities reduced is easily available. Two or more types of the above-mentioned aromatic dihydroxy compounds may be used in combination if necessary.

The diaryl carbonate used in the method for producing an aromatic polycarbonate resin of the present invention is specifically a diaryl carbonate which is represented by the following formula (6):

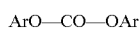
(6)

wherein Ar is as defined above, and which contains a compound of the following formula (I):

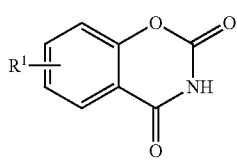

wherein $R^1$ is as defined above
in an amount of less than 1,000 ppm by mass.

As a specific example of the diaryl carbonate, there can be mentioned diphenyl carbonate which contains the compound of the formula (I) wherein $R^1$ is a hydrogen atom (2H-1,3-benzoxazine-2,4(3H)-dione) in an amount of less than 1,000 ppm by mass.

In the method for producing an aromatic polycarbonate resin, the diaryl carbonate may be used in an excess amount with respect to the amount of the aromatic dihydroxy compound.

In the method for producing an aromatic polycarbonate resin, the polycondensation reaction of the aromatic dihydroxy compound and diaryl carbonate is conducted in the presence of a catalyst. With respect to the catalyst, a transesterification catalyst, such as a basic compound catalyst used as a catalyst for general polycarbonate production, can be used.

The catalyst is preferably at least one member selected from the group consisting of an alkali metal compound and an alkaline earth metal compound. At least one member selected from the group consisting of cesium carbonate, sodium hydrogencarbonate, sodium tetraphenylborate, disodium phenylphosphate, and potassium carbonate is more preferably used, and at least one of cesium carbonate and potassium carbonate is further preferably used. The catalysts can be used individually or in combination.

The catalyst may be used in an arbitrary amount, for example, in a ratio of $1 \times 10^{-6}$ mol or less, relative to 1 mol of (the total of) the aromatic dihydroxy compound(s).

It is preferred that the method for producing an aromatic polycarbonate resin is performed in the presence of a promoter as well as a catalyst (preferably, at least one member selected from the group consisting of an alkali metal compound and an alkaline earth metal compound). By using a promoter, it is possible to more efficiently produce an aromatic polycarbonate resin.

With respect to the promoter, a nitrogen-containing compound for use as a transesterification catalyst is preferably used. Details of the nitrogen-containing compound are as mentioned above. With respect to the promoter, specifically, at least one member selected from the group consisting of quaternary ammonium hydroxides is preferably used, at least one member selected from the group consisting of tetraalkylammonium hydroxides is more preferably used, and tetramethylammonium hydroxide is further preferably used.

With respect to the amount of the promoter used, the promoter may be used in an arbitrary amount, preferably, for example, $1 \times 10^{-3}$ mol or less, relative to 1 mol of (the total of) the aromatic dihydroxy compound(s).

In the method for producing an aromatic polycarbonate resin, it is preferred that the aromatic dihydroxy compound and diaryl carbonate, which are main raw materials, are subjected to polycondensation reaction in the presence of a catalyst in a polycondensation reactor to produce an aromatic polycarbonate resin. This polycondensation reaction is a melt polycondensation reaction based on a transesterification reaction.

With respect to the polycondensation reactor used for practicing the method for producing an aromatic polycarbonate resin, one or two or more reactors are used. When two or more reactors are used, the reactors may be connected in series. The polycondensation reactor may be either of a vertical type or of a horizontal type.

Each polycondensation reactor can be provided with an agitation apparatus, such as a conventionally known agitating blade. Specific examples of agitating blades include an anchor agitator blade, a Maxblend impeller, a double helical ribbon blade, a lattice blade, and a spectacle-shaped blade.

It is preferred that the reaction conditions in the polycondensation reactor are set so that the temperature becomes higher, the degree of vacuum becomes higher, and the stirring speed becomes lower as the polycondensation reaction proceeds. It is preferred that the liquid level in each reactor is controlled so that the average residence time in each reactor becomes about 30 to 120 minutes during the polycondensation reaction. Further, in each reactor, phenol which is by-produced concurrently with the melt polycondensation reaction may be distilled off from the system through a distillate tube provided in each reactor.

In the method for producing an aromatic polycarbonate resin, the degree of vacuum is preferably 1 Pa to 13.3 kPa, and the inner temperature in the reactor is preferably 140 to 300° C.

EXAMPLES

Hereinbelow, the present invention will be described in more detail with reference to the following Examples, which should not be construed as limiting the scope of the present invention.

(Measurement of a BOD Concentration)

Each of the samples (BOD-containing DPC) obtained in Examples 1 to 10 was dissolved in acetone, and heptylbenzene as an internal standard material was added to the resultant solution, and subjected to quantitative determination by means of a gas chromatography analysis apparatus under the below-shown conditions for measurement. Substantially the same procedure as mentioned above was repeated to prepare sample solutions having respective known concentrations, and a calibration curve was prepared using the prepared solutions, and used in an analysis for a BOD concentration in DPC.

<Conditions for Measurement>

Measuring apparatus: Shimadzu GC-2014
Detector: FID
Column: GL Sciences Inc. TC-17 (0.30 m×0.25 mm I.D.),
Column temperature: 70° C. (5 min)—12° C./min—190° C. (5 min)–12° C./min—250° C. (30 min)
Injection temperature: 250° C.
Detection temperature: 260° C.
Inlet pressure: 123.8 kPa
Column flow rate: 1.53 ml/min
Linear velocity: 35.5 cm/s
Total flow rate: 81.9 ml/min
Injection mode: SPLIT
Control mode: Linear velocity
Carrier gas: He Examples 1 to 6 and Comparative Examples 1 to 4

(Dibutyl Carbonate (DBC) Synthesis Step)

Using four continuous reaction vessels each equipped with a reflux condenser and a stirrer, urea, butanol (BuOH), diphenyl ether (DPE), and dibutyltin oxide (catalyst) in a [1:2:4:0.05] molar ratio were individually continuously fed at 126 kg/h to the first vessel, and a reaction was conducted under conditions such that the reaction mixture temperatures in the respective vessels became as follows: the first vessel: 170° C.; the second vessel: 180° C.; the third vessel: 190° C., and the fourth vessel: 200° C., and the average residence time in each vessel became 2 hours while withdrawing the formed ammonia from the upper portion of the reflux condenser, so that a liquid containing DBC and butyl carbamate (BCM) was continuously obtained from the fourth vessel.

The obtained liquid was subjected to distillation in a catalyst separation column, so that a liquid comprised mainly of DPE and the catalyst was first withdrawn from the bottom of the column, and a liquid containing a part of DPE, DBC, BCM, and BuOH was withdrawn from the top of the column.

Then, the liquid withdrawn from the top of the catalyst separation column was subjected to distillation in a BuOH separation column, so that BuOH was withdrawn from the top of the column and a liquid containing DPE, DBC, and BCM was withdrawn from the bottom of the column.

Further, phenol (PhOH) was added to the liquid withdrawn from the bottom of the butanol separation column, wherein the amount of the phenol added is twice the mole of the DBC contained in the withdrawn liquid, and the resultant mixture was subjected to distillation in a BCM separation column, so that a liquid containing: DBC: 48.0% by mass; PhOH: 51.9% by mass; and BCM: 0.1% by mass was obtained from the top of the column.

(Transesterification Step by Reactive Distillation)

0.4 Part by mass of titanium tetrabutoxide (transesterification catalyst) was added to the liquid containing: DBC: 48.0% by mass; PhOH: 51.9% by mass; and BCM: 0.1% by mass, and the resultant mixture was continuously fed to the highest plate of a reactive distillation column for transesterification.

In this instance, vapor containing BuOH formed in the transesterification reaction was continuously withdrawn from the top of the reactive distillation column for transesterification, and, meanwhile, a liquid containing butylphenyl carbonate (BPC) formed in the transesterification reaction was continuously withdrawn from the bottom of the column.

(Disproportionation Step)

The liquid withdrawn from the bottom of the reactive distillation column for transesterification was fed to the middle portion of a reactive distillation column for disproportionation, and DBC was continuously withdrawn from the top of the column, and a mixture containing DPC, the transesterification catalyst, BPC, and BOD was continuously withdrawn from the bottom of the column.

(Purification Step)

<Catalyst Separation Step and BPC Recovery Step>

The reaction mixture obtained from the bottom of the column in the disproportionation step was first subjected to distillation in a catalyst separation column, and the catalyst and a part of DPC were continuously withdrawn from the bottom of the column, and a liquid containing mainly DPC and BPC was withdrawn from the top of the column.

Then, the liquid withdrawn from the top of the catalyst separation column was fed to the middle portion of a BPC separation column, so that a liquid comprised mainly of BPC was obtained from the top of the column and a mixture containing DPC and BOD (DPC: 99.49% by mass; 2H-1,3-benzoxazine-2,4(3H)-dione (BOD): 0.51% by mass) was obtained from the bottom of the column.

<Distillation Step>

The mixture obtained from the bottom of the BPC separation column was fed to the 4th plate of a distillation column packed with Sulzer packing, in which the number of theoretical plates was 8, the column bottom temperature was 188.5° C., and the column top pressure was 2 kPa, so that the mixture was subjected to distillation with different reflux ratios, obtaining DPC from the top of the column. The BOD concentration in the obtained DPC (column top DPC) is shown in Table 1.

TABLE 1

| | | | Example 1 | Example 2 | Example 3 | Example 4 | Example 5 | Example 6 | Comparative Example 1 | Comparative Example 2 | Comparative Example 3 | Comparative Example 4 |
|---|---|---|---|---|---|---|---|---|---|---|---|---|
| DPC Purification | Feed rate | kg/h | 15 | 15 | 15 | 15 | 14 | 20 | 30 | 40 | 15 | 15 |
| | Column top pressure | KPaA | 2.9 | 2.9 | 2.9 | 2.9 | 2.9 | 2.8 | 3 | 2.9 | 2.9 | 2.9 |
| | Reflux ratio | R/D | 20 | 15 | 9 | 4 | 3 | 2 | 1 | 0.5 | 0.1 | 0 |
| BOD Concentration in column top DPC | LC Composition | ppm | 0.3 | 3 | 30 | 300 | 600 | 900 | 1300 | 1700 | 3000 | 5100 |

Examples 7 to 30

<Precipitation Step>

The distillation step in each Example was performed until the compound of the formula (I) in the liquid in the vessel was built up in such a concentration that the compound was precipitated when the temperature at the bottom of the column was reduced to 188.5° C. or lower. The resultant liquid in the vessel was withdrawn and then cooled so that the compound of the formula (I) was precipitated, followed by filtration under reduced pressure using No. 5C filter paper having a diameter of 330 mm, manufactured by Advantech Toyo Kaisha, Ltd., recovering a filtrate. The concentrations of the compound of the formula (I) and the precipitation conditions in the respective procedures are shown in Table 2. The solubility of BOD in DPC was measured and found to be as shown in FIG. 1.

TABLE 2

| | | | Example | | | | | | | | | | | |
|---|---|---|---|---|---|---|---|---|---|---|---|---|---|---|
| | | | 7 | 8 | 9 | 10 | 11 | 12 | 13 | 14 | 15 | 16 | 17 | 18 |
| Example for distillation step | | | 1 | 2 | 3 | 4 | 5 | 6 | 1 | 2 | 3 | 4 | 5 | 6 |
| BOD Concentration in column bottom DPC | GC Composition | wt % | 25.9 | 25.5 | 24.8 | 23.3 | 22.6 | 21.4 | 25.9 | 25.5 | 24.8 | 23.3 | 22.6 | 21.4 |
| Precipitation temperature | | °C. | 82 | 82 | 82 | 82 | 82 | 82 | 100 | 100 | 100 | 100 | 100 | 100 |
| BOD Concentration in filtrate DPC | GC Composition | ppm | 4119 | 4115 | 4116 | 2120 | 4122 | 4118 | 11631 | 11635 | 11636 | 11635 | 11632 | 11634 |

| | | | Example | | | | | | | | | | | |
|---|---|---|---|---|---|---|---|---|---|---|---|---|---|---|
| | | | 19 | 20 | 21 | 22 | 23 | 24 | 25 | 26 | 27 | 28 | 29 | 30 |
| Example for distillation step | | | 1 | 2 | 3 | 4 | 5 | 6 | 1 | 2 | 3 | 4 | 5 | 6 |
| BOD Concentration in column bottom DPC | GC Composition | wt % | 25.9 | 25.5 | 24.8 | 23.3 | 22.6 | 21.4 | 25.9 | 25.5 | 24.8 | 23.3 | 22.6 | 21.4 |
| Precipitation temperature | | °C. | 120 | 120 | 120 | 120 | 120 | 120 | 150 | 150 | 150 | 150 | 150 | 150 |
| BOD Concentration in filtrate DPC | GC Composition | ppm | 27899 | 27895 | 27903 | 27899 | 27897 | 27902 | 85595 | 85599 | 85598 | 85596 | 85599 | 85602 |

Example 31

<Recycling Step>

The catalyst separation step and BPC recovery step in the purification step were performed in accordance with the same procedure as in Example 2. Then, the filtrate obtained in the precipitation step in Example 20 was added to the mixture obtained from the bottom of the BPC separation column in the BPC recovery step, and the resultant mixture was subjected to the distillation step in accordance with the same procedure as in Example 2. The BOD concentration (GC composition) of the obtained column top DPC was equivalent to the BOD concentration (GC composition) in Example 2 which includes no recycling.

Examples 32 to 36 and Comparative Example 5

(Evaluation of Polycarbonate Polymerization Activity)

In Examples 32 to 36 and Comparative Example 5, with respect to the DPCs obtained in Examples 1 to 4 and 6 and Comparative Example 3, polycarbonate (PC) polymerization between each DPC and bisphenol A (BPA) was evaluated.

(Raw Materials for Polymerization)

With respect to DPC, those which are shown in Table 1 above for Examples 1 to 4 and 6 and Comparative Example 3 were used, and, with respect to BPA, one which is manufactured by Nippon Steel & Sumikin Chemical Co., Ltd. was used.

(Polymerization Catalyst)

0.15 g of cesium carbonate, manufactured by Wako Pure Chemical Industries, Ltd., was accurately weighed, and dissolved in distilled water using a 100 mL measuring flask to obtain a 0.005 mol/L aqueous solution of cesium carbonate.

(Analysis Method for Molecular Weight)

With respect to the obtained resin, an analysis of a molecular weight was conducted using high-performance GPC apparatus HLC-8320 GPC, manufactured by Tosoh Corp., which is equipped with three columns for ultra-high performance semi-micro SEC, TSKgel SuperMultipore (registered trademark) HZ-M, manufactured by Tosoh Corp., and using a chloroform solvent (for HPLC), manufactured by Wako Pure Chemical Industries, Ltd., under conditions such that the sample concentration was 0.2 w/v %, the flow rate was 0.350 mL/min, and the amount of the sample per injection was 10 μL. A calibration curve was prepared using standard polystyrene kit PStQuick (registered trademark) MP-M, manufactured by Tosoh Corp.

(Measurement of a Terminal OH Amount)

The measurement of a terminal OH amount was performed using Cryo NMR, manufactured by Bruker Corporation. 0.05 g of a sample was dissolved in 1 mL of a 0.05 wt % TMS-added, deuterated chloroform solvent, and subjected to measurement of $^1$H-NMR at a standard frequency of 600 MHz. In the obtained NMR spectrum, the integrated area of a peak ascribed to a phenyl group and a phenylene group appearing at around 7 to 8 ppm was taken as 100, and a ratio of the integrated area of a peak ascribed to a hydroxyl group appearing at around 4.7 ppm to the above integrated area was calculated, and thus a terminal amount was determined from the ratio.

(Analysis for a Yellow Index(YI) Value)

A YI value was measured using colorimeter SE2000, manufactured by Nippon Denshoku Industries Co., Ltd., with respect to 6 g of a sample which was dissolved in 60 mL of a dichloromethane solvent, manufactured by Wako Pure Chemical Industries, Ltd.

(Polymerization Apparatus)

A 300 mL four-neck glass flask was used as a polymerization apparatus, wherein the glass flask has connected thereto a distillation portion made of glass having a connecting tube, an air condenser, an alcohol thermometer and a receiver, and a stirrer for flask having a stainless steel stirring rod and a Teflon (registered trademark) agitating blade. A nitrogen gas introducing tube and a rotary pump were connected to the polymerization apparatus through the connecting tube which connects the receiver and air condenser, enabling the pressure in the polymerization apparatus to be controlled.

(Procedure for Polymerization)

70.0 g of BPA, 69.6 g of DPC (molar ratio of DPC to BPA: 1.06), and 30 µL of a 0.005 mol/L aqueous solution of cesium carbonate as a catalyst were charged into the polymerization apparatus.

Then, for drying the BPA, DPC, and catalyst charged into the polymerization apparatus, while stirring at 4 rpm using the stirrer for flask, drying was performed in a vacuum at 27° C. for one hour. After drying, the pressure in the polymerization apparatus was increased to 97 kPa using nitrogen gas.

A point in time when the flask portion of the polymerization apparatus, which had been dried and increased in the pressure, was immersed in an oil bath set at 205° C. was regarded as a start of polymerization, and the raw materials were melted for 5 minutes while stirring at 4 rpm using the stirrer for flask, and the number of revolutions of the stirrer for flask was increased to 200 rpm, followed by stirring for 5 minutes.

The pressure in the polymerization apparatus was reduced from 97 to 27 kPa for 10 minutes while stirring, and a point in time when the alcohol thermometer of the polymerization apparatus indicated 100° C. was recorded as a time for the start of distilling off of phenol by-produced in the reaction of BPA and DPC.

From a point in time when the amount of the phenol distilled off during the reaction reached 30% of the distilled phenol amount presumed from the amounts of the charged raw materials, the temperature set for the oil bath and the pressure in the polymerization apparatus were changed stepwise according to the distilled phenol amount, and, from a point in time when the distilled phenol amount reached 90% of the presumed amount of the phenol distilled, the temperature of the oil bath was increased to 260° C. and the pressure in the polymerization apparatus was reduced to achieve a vacuum for 10 minutes. In the case where the BOD content in the DPC was 3,000 ppm by mass, the above-mentioned procedure did not cause phenol to be distilled off. Therefore, the temperature set for the oil bath was increased and the pressure in the polymerization apparatus was reduced so as to cause phenol to be distilled off.

After stirring was made in a vacuum at an oil bath temperature of 260° C. for 1.5 hours, the reaction was terminated, and the PC in the polymerization apparatus was recovered. The results shown in Table 3 were obtained according to the BOD content in the DPC used.

In the production of an aromatic polycarbonate resin by a melt transesterification method, by using a diaryl carbonate containing the compound of the formula (I) in an amount of less than 1,000 ppm by mass, the polymerization time can be markedly reduced and an aromatic polycarbonate resin having suppressed the terminal OH group amount can be obtained, as compared to those in the production of an aromatic polycarbonate resin using a diaryl carbonate produced by a conventional method.

What is claimed is:

1. A method for producing a diaryl carbonate composition containing a compound of the following formula (I) in an amount of less than 1,000 ppm by mass:

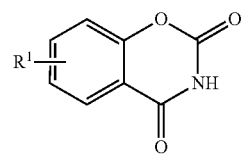

(I)

wherein $R^1$ represents a hydrogen atom, a halogen atom, an alkyl group, an alkoxy group, an aryl group, or an aryloxy group, the method comprising:
(A) reacting urea with an alkyl alcohol to yield a first reaction mixture containing a dialkyl carbonate;
(B) reacting the dialkyl carbonate in the first reaction mixture with an aryl alcohol to yield a second reaction mixture containing an alkylaryl carbonate;
(C) subjecting the alkylaryl carbonate in the second reaction mixture to disproportionation to yield a third reaction mixture containing a diaryl carbonate wherein the third reaction mixture contains the compound of the formula (I) in an amount of 1,000 ppm by mass or more;
(D) purifying the third reaction mixture by using a distillation column, thereby obtaining the diaryl carbonate containing the compound of the formula (I) in an amount of less than 1,000 ppm by mass from the top of the distillation column and obtaining a concentrated mixture comprising the compound of the formula (I) from the bottom of the distillation column, wherein the distillation is conducted under the following conditions (a) and (b):
(a) the pressure at the top of the distillation column is 0.01 to 10 kPa, and
(b) the reflux ratio is 2 to 20;

TABLE 3

|  | Example 32 | Example 33 | Example 34 | Example 35 | Example 36 | Comparative Example 5 |
|---|---|---|---|---|---|---|
|  |  |  | DPC |  |  |  |
|  | Example 1 | Example 2 | Example 3 | Example 4 | Example 6 | Comparative Example 3 |
| BOD Content | 0.3 ppm | 3 ppm | 30 ppm | 300 ppm | 900 ppm | 3000 ppm |
| Start of distilling | 27 min. | 29 min. | 31 min. | 42 min. | 71 min. | *1 |
| 30% Distilled | 60 min. | 60 min. | 70 min. | 100 min. | 180 min. | *1 |
| 90% Distilled | 190 min. | 190 min. | 200 min. | 235 min. | 325 min. | *1 |
| Mw | 31,000 | 31,000 | 26,000 | 22,000 | 17,000 | 9,000 |
| Terminal OH amount | 216 ppm | 394 ppm | 650 ppm | 451 ppm | 523 ppm | 2702 ppm |
| Solution YI | — | 1.51 | 1.52 | 1.50 | 1.60 | 1.81 |

*1: The temperature of the oil bath and the pressure in the polymerization apparatus were changed to cause a phenol to be distilled off (E) filtering off the compound of the formula (I) which is precipitated from the concentrated mixture at a temperature in the range of from 80 to 230° C., and (F) recovering the compound of the chemical formula (I) filtered off in (E) and bringing the filtrate back to (D).

2. The method according to claim 1, wherein the alkyl alcohol used in (A) is an alkyl alcohol having 3 to 6 carbon atoms.

3. A method for producing an aromatic polycarbonate resin, the method comprising producing the diaryl carbonate according to claim 1, and performing melt polycondensation of the diaryl carbonate and an aromatic dihydroxy compound in the presence of a transesterification catalyst that catalyzes the melt polycondensation.

* * * * *